United States Patent [19]
Dehoux et al.

[11] Patent Number: 5,958,687
[45] Date of Patent: Sep. 28, 1999

[54] NUCLEOTIDE SEQUENCES AND PROTEINS CONFERRING CYCLOHEXIMIDE RESISTANCE

[75] Inventors: Pierre Dehoux; Julian Davies, both of Paris, France

[73] Assignee: Institut Pasteur, Paris Cedex, France

[21] Appl. No.: 08/818,726

[22] Filed: Mar. 14, 1997

Related U.S. Application Data

[63] Continuation of application No. 08/175,388, filed as application No. PCT/FR92/00685, Jul. 15, 1992, Pat. No. 5,641,674.

[30] Foreign Application Priority Data

Jul. 15, 1991 [FR] France ..................... 9108906

[51] Int. Cl.$^6$ .............. C12Q 1/68; C12N 1/14; C12N 15/00; C07H 21/04
[52] U.S. Cl. ............ 435/6; 435/254.2; 435/320.1; 435/325; 435/419; 530/371; 530/350; 536/23.74
[58] Field of Search ................. 536/23.2, 24.1, 536/23.74; 435/6, 254.1, 254.2, 325, 419, 320.1; 530/371

Primary Examiner—Ponnathapura Achutamurthy
Assistant Examiner—Tekchand Saidha
Attorney, Agent, or Firm—Oblon, Spivak, McClelland, Maier & Neustadt, P.C.

[57] ABSTRACT

The invention relates to a nucleotide sequence coding for a cycloheximide resistance protein sensitive to concatenation of amino acids A, or coding for all or part of said optionally modified concatenation A, in as much as the formed protein confers cycloheximide resistance to a recombinant eucaryotic host transformed by the nucleotide sequence coding for said protein, in conditions appropriate for its production. The invention also relates to a sequence containing the DNA coding for the concatenation A and capable of conferring a high level of resistance to cycloheximide in a given host.

18 Claims, 5 Drawing Sheets

```
                  10          20          30          40          50          60
       1   CCTCGAGGTC GACATTCAAG GGTTTAGTAT CCTGAAAACA AAGCTTGTAT AGACAGCCGA    60
      61   CGGTTCTTGG TGACTGTTTG CATCCGTGCA CCATAAAATC TCTCTTAACC ACCCACACAT   120
     121   TGATTTTCGT GTCAATTGAA AATGTGAAAA ATAAAATTGT TCCCAATTA  GGACTATATT   180
     181   CGTCTGTGGG AAAATAACAT TGCCTAGTGG CATTGGTGTG GCCTAACCAG GCCGAATCAC   240
     241   TCACTTTCCA CTAACAGACC TTCCTCCTGG TCGGTCTGGT CTGCTTCTG  GGCAGTGTAG   300
     301   TCTCTCTTGC CAACACATTA CGCATTCATG GTCGGGGGC  CAGTAACGCC TGCTCGTCTG   360
     361   GCTAAGCTTG GACGTGCGTA GTCGCCGTC  TCTGCTTCGA TGGCTGCCAT TCGGCAATTC   420
     421   CCTTCACTCT TGCTCACTCT AAAATATTAC AAAATATTAC ACAAGGAAAG TTCATCATAG   480
     481   GGATTGAACC ACCTTGAATT TTCAACATT  AAAATATTAC ACAAGGAAAG TTCATCATAG   540
     541   TAGATATATC GTATAGTTGA TTGTTATAGC ACCTATTTGT TTCAGTACAT TCAGAAAGCG   600
     601   TAACTCAACA GAGATCAAAT CAGTCACAAT GGGTATGTGA ACAAGATTTA AAATATACCG   660
     661   TGGAGATTGT CAGTGGTTTA TTCGATTTTT GGTATCCTGA GGGAAGAATG GAACGTTTGA   720
     721   AGTTAGTAC  CAAGTGAACA TGAAATGAGC TATGGTTATT TAACAGAATA CAGCATTTCA   780
     781   GAGTGAATCA ATGAGAAAAC ACCAACCGTA TTGGAAATTC AGATATTGCA TCGACAAGGG   840
     841   GGGAGAGTTC ATTTGAGTTG GTGAACTATA TCAAAAGATC AGTATTTTGG TCGAAGTATG   900
     901   GACGATTCAC TAGCATAAAA CCCTGTTCAC GCTGGAGGAA GTAATGTGGG TTATTTGTTG   960
     961   TCCCTATGTT TCTTAATTCG GTGTAGTCGA GACAACCTCA GAGAATTGTA TATCAGTGAA  1020
    1021   GTCAACGCTA CACTGACTGA ACATAATTAA CAGGAACTCA GTCGTATTAA ACAACTGGGG  1080
    1081   TTCAGATAGC CTGGACCTCC CTATACAATA AGAAGAAGAG AATAGAATTC CTGCAATCAA  1140
    1141   AATAAGCTGG ATGAAGCTAA AGAATATTTT TTTACTAACA AGAATATTTT TCGACATGTA TCACTATCTT  1200
```

```
1201  ATGATATGTT AATTCTAAC AGTTAACGTT CCAAAGACCA GAAAGACTTA CTGTAAGGGT  1260
1261  AAGGAGTGCC GTAAGCACGC CCAACACAAG GTACCCAAT  ACAAGGCTGG TAAGGCTTCC  1320
1321  TTGTACGCTC AAGGTAAGAG AAGATATGAC CGTAAACAAT CTGGTTTCGG TGGTCAAACC  1380
1381  AAGCAAATTT TCCACAAGAA AGCTAAGACT ACCAAGAAGG TCGTTTTGAG ATGGAATGT   1440
1441  ATGTCCTGTA AGACCAAGAC CCAATTGGCT TTGAAGAGAT GTAAGCACTT CGAATGGGT   1500
1501  GGTGAAAAGA AGCAAAAAGG TCAAGCTTTG CAATTCTGAG ATTATCTTTT GGAAGACCAT  1560
1561  TTGTTACCAA TTTGTCAATT TTTAACTTT  TCTATAAGTA TTACGAATTC ACATATACTC  1620
1621  TTTCATCACA TTTATAATCT CATATCTGTC ATTGTATAG  TTTAGTCTCC ACTGGGTACT  1680
1681  TCTTCACTTT GCGATTTGTA TTATACGTAT TCTAAGTATA ATTTTCAGCA GAACGCATAA  1740
1741  GAGTTTATTA ACAAGAATTG TTTACAAAGA ATAGCGTAGG ACTCAGGCTA CATTATTGAT  1800
1801  CCTGCAGGCA GTAAAGCTTA CATATGACCT TAGCTAATAT AACATGTACA TACTCACCAT  1860
1861  GTATACCACT TTTTTCATTC CATTGTCTAA AATATGTTTT CAAACTTGTT CAAAATCGCC  1920
1921  AATTTCATTG GAAAAACAAA AACATCGAAT CAAACTTGTT TTAGAAAACA ACGAACATGA  1980
1981  AACTATACTG TTAACGTTTA GAGACATATT TCACGTCAAC AAGGCCGTTT GGACGTCGCT  2040
2041  ACTTCAGCAA CAACACGTAA TGTACGGTGG ATATTCGAAT CAGAACTACT ATCAACAGCC  2100
2101  TTCTGGTCGT CCGAAACGAT TTCAGCAAC  AGGGAAACAT GCCCTTTTCG GAACCTTCTC  2160
2161  AGCCCATGTT CAGCACCAAT TATATGAAAC AACAAGGATC ACAGCCGTCT TACAAGACCG  2220
2221  TCTGACCCAA CAGCAATCGC AACCTCAGTC GCATAATAAT CAATATTATC CGAATGGAGG  2280
2281  GTTTACTGAT GTGCCCAACT TGAATTATCC AGGGACTCCA CCACCAACTC AAAGCATTTA  2340
```

```
2341  TTCACATAAC AACAACTCTA ATTCGAAGGT ATATCAATCC GCTCAGCATA CATCTCCCGG  2400
2401  TCAATATTCT GTTGCCAGTG AGTCCGGTTT GTACATCCCG CCACCACTGC AGCAACAGCA  2460
2461  GAATGGTCAA CAGAGTCCTG TGAGATCGGT ACATCAACAG ACACAGCAAA CACCGCCAAC  2520
2521  ATTTACTCAG CAACAAAGCT CTCCCCAACC TCAGTCACCT CAACACAATA CGTTATCATG  2580
2581  CACAGCAGCA GCAGCAGCAG CAGTCTCAGC AACAACAAAC TCAACAGGCC CAGCAGCAAG  2640
2641  GACAACGACA AACTCAGCAA CAGTCTCAGC AGCAAGCTCA ACAACAGAAT GGATCGGCGA  2700
2701  ATAATTACAT GTATTTTGAG AGAAGACCTG ACCTATTGAC CAAAACTACC CAAGACAAAG  2760
2761  CAGATCGAAT TCCTGCAGCC CGGGGATCC ACTAGTTCTA GAGCGGCCGC CACCGCGGTG  2820
2821  GAGCTCCAAT TCGCCCTATA GT                                          2842
          |         |         |         |         |         |
         10        20        30        40        50        60
```

*FIG. 2C*

1/1                          31/11
Met val asn val pro lys thr arg lys thr tyr cys lys gly lys glu cys arg lys his 61/21                         91/31
ala gln his lys val thr gln tyr lys ala gly lys ala ser leu tyr ala gln gly lys 121/41                        151/51
arg arg tyr asp arg lys gln ser gly phe gly gly gln thr lys gln ile phe his lys 181/61                        211/71
lys ala lys thr thr lys lys val val leu arg leu glu cys met ser cys lys thr lys 241/81                        271/91
thr gln leu ala leu lys arg cys lys his phe glu leu gly gly glu lys lys gln lys 301/101
gly gln ala leu gln phe OPA

*FIG. 4*

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 106 amino acids
      (B) TYPE: amino acid
      (C) STRANDEDNESS: single
      (D) TOPOLOGY: unknown    (ii) MOLECULE TYPE: protein    (xi) SEQUENCE DESCRIPTION: SEQ ID NO:1:

```
Met Val Asn Val Pro Lys Thr Arg Lys Thr Tyr Cys Lys Gly Lys Glu
1               5                   10                  15

Cys Arg Lys His Ala Gln His Lys Val Thr Gln Tyr Lys Ala Gly Lys
                20                  25                  30

Ala Ser Leu Tyr Ala Gln Gly Lys Arg Arg Tyr Asp Arg Lys Gln Ser
            35                  40                  45

Xaa Phe Gly Gly Gln Thr Lys Gln Ile Phe His Lys Lys Ala Lys Thr
        50                  55                  60

Thr Lys Lys Val Val Leu Arg Leu Glu Cys Met Ser Cys Lys Thr Lys
65                  70                  75                  80

Thr Gln Leu Ala Leu Lys Arg Cys Lys His Phe Glu Leu Gly Gly Glu
                85                  90                  95

Lys Lys Gln Lys Gly Gln Ala Leu Gln Phe
                100                 105
```

(2) INFORMATION FOR SEQ ID NO:2:

(i) SEQUENCE CHARACTERISTICS:
      (A) LENGTH: 321 base pairs
      (B) TYPE: nucleic acid
      (C) STRANDEDNESS: unknown
      (D) TOPOLOGY: unknown    (ii) MOLECULE TYPE: DNA (genomic)

(xi) SEQUENCE DESCRIPTION: SEQ ID NO:2:

```
ATGGTTAACG TTCCAAAGAC CAGAAAGACT TACTGTAAGG GTAAGGAGTG CCGTAAGCAC      60

GCCCAACACA AGGTTACCCA ATACAAGGCT GGTAAGGCTT CCTTGTACGC TCAAGGTAAG     120

AGAAGATATG ACCGTAAACA ATCTGGTTTC GGTGGTCAAA CCAAGCAAAT TTTCCACAAG     180
```

| AAAGCTAAGA CTACCAAGAA GGTCGTTTTG AGATTGGAAT GTATGTCCTG TAAGACCAAG | 240 |
| ACCCAATTGG CTTTGAAGAG ATGTAAGCAC TTCGAATTGG GTGGTGAAAA GAAGCAAAAG | 300 |
| GGTCAAGCTT TGCAATTCTG A | 321 |

(2) INFORMATION FOR SEQ ID NO:3:

(i) SEQUENCE CHARACTERISTICS:
        (A) LENGTH: 2842 base pairs
        (B) TYPE: nucleic acid
        (C) STRANDEDNESS: double
        (D) TOPOLOGY: unknown     (ii) MOLECULE TYPE: DNA (genomic)

(xi) SEQUENCE DESCRIPTION: SEQ ID NO:3:

| CCTCGAGGTC GACATTCAAG GGTTTAGTAT CCTGAAAACA AAGCTTGTAT AGACAGCCGA | 60 |
| CGGTTCTTGG TGACTGTTTG CATCCGTGCA CCATAAAATC TCTCTTAACC ACCCACACAT | 120 |
| TGATTTTCGT GTTCAATTGA AATGTGAAAA ATAAAATTGT TTCCCAATTA GGACTATATT | 180 |
| CGTCTGTGGG AAAATAACAT TGCCTAGTGG CATTGGTGTG GCCTAACCAG GCCGAATCAC | 240 |
| TCACTTTCCA CTAACAGACC TTCCTCCTGG TCGGTCTGGT CTGGGCTACC GGCAGTGTAG | 300 |
| TCTCTCTTGC CAACACATTA CGCATTCATG CTTGCTTCTG CCTACTGCTT CCCCGCCCAG | 360 |
| GCTAAGCTTG GACGTGCGTA GTCGGGGGGC CAGTAACGCC TGCTCGTCTG GACTTGTTCG | 420 |
| CCTTCACTCT TGCTGCCGTC TCTGCTTCGA TGGCTGCCAT TCGGCAATTC TCATCTGGAA | 480 |
| GGATTGAACC ACCTTGAATT TTTCAACATT AAAATATTAC ACAAGGAAAG TTCATCATAG | 540 |
| TAGATATATC GTATAGTTGA TTGTTATAGC ACCTATTTGT TTCAGTACAT TCAGAAAGCG | 600 |
| TAACTCAACA GAGATCAAAT GAGTCACAAT GGGTATGTGA ACAAGATTTA AAATATACCG | 660 |
| TGGAGATTGT CAGTGGTTTA TTCGATTTTT GGTATCCTGA GGGAAGAATG GAACGTTTGA | 720 |
| AGTTTAGTAC CAAGTGAACA TGAAATGAGC TATGGTTATT TAACAGAATA CAGCATTTCA | 780 |
| GAGTGAATCA ATGAGAAAAC ACCAACCGTA TTGGAAATTC AGATATTGCA TCGACAAGGG | 840 |
| GGGAGAGTTC ATTTGAGTTG GTGAACTATA TCAAAAGATC AGTATTTTGG TCGAAGTATG | 900 |
| GACGATTCAC TAGCATAAAA CCCTGTTCAC GCTGGAGGAA GTAATTTGGG TTATTTGTTG | 960 |
| TCCCTATGTT TCTTAATTCG GTGTAGTCGA GACAACCTCA GAGAATTGTA TATCAGTGAA | 1020 |
| GTCAACGCTA CACTGACTGA ACATAATTAA CAGGAACTCA GTCGTATTAA CAACTGGGG | 1080 |
| TTCAGATAGC CTGGACCTCC CTATACAATA AGAAGAAGAA AATAGAATTC CTGCAATCAA | 1140 |
| AATAAGCTGG ATGAAGCTAA AGAATATTTT TTTACTAACA TCGACATGTA TCACTATCTT | 1200 |
| ATGATATGTT AATTTCTAAC AGTTAACGTT CCAAAGACCA GAAAGACTTA CTGTAAGGGT | 1260 |
| AAGGAGTGCC GTAAGCACGC CCAACACAAG GTTACCCAAT ACAAGGCTGG TAAGGCTTCC | 1320 |
| TTGTACGCTC AAGGTAAGAG AAGATATGAC CGTAAACAAT CTGGTTTCGG TGGTCAAACC | 1380 |
| AAGCAAATTT TCCACAAGAA AGCTAAGACT ACCAAGAAGG TCGTTTTGAG ATTGGAATGT | 1440 |
| ATGTCCTGTA AGACCAAGAC CCAATTGGCT TTGAAGAGAT GTAAGCACTT CGAATTGGGT | 1500 |
| GGTGAAAAGA AGCAAAAGGG TCAAGCTTTG CAATTCTGAG ATTATCTTTT GGAAGACCAT | 1560 |
| TTGTTACCAA TTTGTCAATT TTTTAACTTT TCTATAAGTA TTACGAATTC ACATATACTC | 1620 |
| TTTCATCACA TTTATAATCT CATATCTGTC ATTTGTATAG TTTAGTCTCC ACTGGGTACT | 1680 |
| TCTTCACTTT GCGATTGTA TTATACGTAT TCTAAGTATA ATTTTCAGCA GAACGCATAA | 1740 |
| GAGTTTATTA ACAAGAATTG TTTACAAAGA ATAGCGTAGG ACTCAGGCTA CATTATTGAT | 1800 |
| CCTGCAGGCA GTAAAGCTTA CATATGACCT TAGCTAATAT AACATGTACA TACTCACCAT | 1860 |

```
GTATACCACT TTTTTCATTC CATTGTCTAA AATATGTTTT CAATATTTGC CAAAATCGCC     1920

AATTTCATTG GAAAAACAAA AACATCGAAT CAAACTTGTT TTAGAAAACA ACGAACATGA     1980

AACTATACTG TTAACGTTTA GAGACATATT TCACGTCAAC AAGGCCGTTT GGACGTCGCT     2040

ACTTCAGCAA CAACACGTAA TGTACGGTGG ATATTCGAAT CAGAACTACT ATCAACAGCC     2100

TTCTGGTCGT CCGAAACGAT TTTCAGCAAC AGGGAAACAT GCCCTTTTCG GAACCTTCTC     2160

AGCCCATGTT CAGCACCAAT TATATGAAAC AACAAGGATC ACAGCCGTCT TACAAGACCG     2220

TCTGACCCAA CAGCAATCGC AACCTCAGTC GCATAATAAT CAATATTATC CGAATGGAGG     2280

GTTTACTGAT GTGCCCAACT TGAATTATCC AGCGACTCCA CCACCAACTC AAAGCATTTA     2340

TTCACATAAC AACAACTCTA ATTCGAAGGT ATATCAATCC GCTCAGCATA CATCTCCCGG     2400

TCAATATTCT GTTGCCAGTG AGTCCGGTTT GTACATCCCG CCACCACTGC AGCAACAGCA     2460

GAATGGTCAA CAGAGTCCTG TGAGATCGGT ACATCAACAG ACACAGCAAA CACCGCCAAC     2520

ATTTACTCAG CAACAAAGCT CTTCCCAACC TCAGTCACCT CAACACAATA CGTTATCATG     2580

CACAGCAGCA GCAGCAGCAG CAGCAGCAGC AACAACAAAC TCAACAGGCC CAGCAGCAAG     2640

GACAACGACA AACTCAGCAA CAGTCTCAGC AGCAAGCTCA ACAACAGAAT GGATCGGCGA     2700

ATAATTACAT GTATTTTGAG AGAAGACCTG ACCTATTGAC CAAAACTACC CAAGACAAAG     2760

CAGATCGAAT TCCTGCAGCC CGGGGGATCC ACTAGTTCTA GAGCGGCCGC CACCGCGGTG     2820

GAGCTCCAAT TCGCCCTATA GT                                              2842
```

NUCLEOTIDE SEQUENCES AND PROTEINS CONFERRING CYCLOHEXIMIDE RESISTANCE

This is a Continuation of application Ser. No. 08/175,388 filed on Jun. 9, 1994, which was filed as International Application No. PCT/FR92/00685 filed on Jul. 15, 1992 now U.S. Pat. No. 5,641,674.

The invention relates to nucleotide sequences capable of conferring resistance to cycloheximide, cyclheximide resistance proteins and their use as selection markers, for example, to monitor nucleic acid transfer.

The inventors have, in fact, investigated selectionmarkers suitable for monitoring nucleic acid transfer in eukaryotes, markers which might be more efficient than the markers usually used which are derived from prokaryotic organisms. It is know for example that the markers usually used (geneticin G-418, hygromycin and bleomycin) are derived from resistance genes isolated from prokaryotes and are usually rather inefficient, particularly in fungi. These problems oblige experimenters to use very high concentrations of antibiotics which cause toxicity problems and increase production costs. Consequently, other selection agents have been used, for example selection by methotrexate, selection by auxotrophy, etc. However, these selection agents are not generally applicable. There is thus a need for the creation of systems suited to the use of a more efficient and/or potent marker than the markers known hitherto and at lower production costs.

Cycloheximide might constitute a potentially useful marker for example for detecting the transfer of heterologous nucleic acid in eukaryotes. For this purpose, the eukaryotes which it is desired to modify in a controllable manner by means of a detection test for resistance to cycloheximide, must be made resistant to this antibiotic under satisfactory conditions in order to ensure reliable monitoring of the transfer of a heterologous nucleic acid made either for research purposes or for the purpose of industrial exploitation.

Cycloheximide is an antibiotic which inhibits protein synthesis by binding to the 60S ribosomal subunit as described by STOCKLEIN et al. (1980, Curr. Genetics 1, 177–183).

Eukaryotic organisms naturally resistant to cycloheximide are rare; up to now observations relating to the mechanisms of resistance have been described in a mutant of an organism naturally sensitive to cycloheximide, the cyh2 mutant of the yeast *Saccharomyces cerevisiae*. In this context, the phenomenon of resistance is created by a modification of the ribosomal protein L29 (STOCKLEIN et al., 1980).

These mutant cellular organisms are usually resistant to low concentrations of cycloheximide (of the order of 5–10 µg/ml).

Other authors (TAKAGI et al. in the U.S. Pat. No. 4,857,460) have reported results relating to the study of resistance to cycloheximide in another yeast *Candida maltosa*. They present a DNA sequence conferring resistance to cycloheximide on *C. maltosa*. However, neither gene nor open reading frame was identified in this sequence. In other words, the U.S. Pat. No. 4,857,460 does not give the elements for the characterization of a gene, elements which could have led to a definition of the conditions for its use, for example, to transform eukaryotes different from *Candida maltosa* into strains resistant to cycloheximide in a reproducible manner.

The inventors have concerned themselves with the yeast *Kluyveromyces lactis* (*K. lactis*) and demonstrated the fact that cycloheximide resistance in *K. lactis* depends on the expression of a specific gene. They have also identified the fact that the level of resistance of this yeast to this antibiotic involves other elements linked to the presence of a specific DNA which has the role of cofactor (or cofactor sequence).

In an advantageous embodiment of the invention, the resistance obtained is specific for cycloheximide, the transformed hosts resistant to this antibiotic ($cyc^R$) being sensitive to several classical inhibitors of ribosomal functions (cryptopleurin, blasticidin, trichodermin, anisomycin, hygromycin).

Thus the inventors obtained in *K. lactis* a nucleic acid sequence of about 5.2 kb, capable of conferring a level of resistance to a cell host transformed by this sequence sufficiently high for the creation of a selection system as a result of resistance to this antibiotic, this resistance being expressed at a cycloheximide concentration higher than 1 mg/ml.

Within this nucleic acid sequence the inventors have identified and characterized a specific gene coding for a protein whose presence proves to be necessary for inducing the phenomenon of resistance in *K. lactis*.

This specific gene codes for a ribosomal protein which is responsible for resistance to a cycloheximide concentration of the order of 100 µg/ml. Complete resistance to this antibiotic in *K. lactis* requires not only the presence of this resistance-inducing sequence but also the presence of additional DNA elements contained in the 5.2 kb nucleic acid sequence defined by the inventors and described hereafter. These additional elements play the role of cofactors.

Thus, the subject of the present application is nucleotide sequences as well as a protein which are capable of conferring cycloheximide resistance on a eukaryote cell host naturally sensitive to this antibiotic or resistant to a low concentration of this antibiotic (also designated as low-level resistant organism). This first type of protein will be designated in what follows by the expression "resistance protein".

The invention also relates to a nucleic acid sequence comprising a gene which codes for the resistant protein described above in *K. lactis*, as well as sequences determining the presence of cofactors implicated in the level of resistance conferred by the above-mentioned protein.

It also relates to the gene coding for the resistance protein and the different nucleic acid fragments determining the presence of the cofactors.

It also relates to cloning and/or expression vectors for these nucleotide sequences as well as eukaryotic cell hosts transformed by these vectors.

A first protein according to the invention or cycloheximide resistance protein is a protein whose presence is necessary and sufficient to confer resistance to cycloheximide on a host naturally sensitive to it. It is characterized in that it corresponds to the following amino acid sequence A (SEQ ID NO:1), or in that it comprises all or part of this sequence A (SEQ ID NO:1), possibly modified, provided that the protein formed confers cycloheximide resistance on a recombinant eukaryotic host transformed by the nucleotide sequence coding for this protein under conditions allowing its production.

SEQUENCE A:

```
1/1                                     31/11
Met val asn val pro lys thr arg lys thr tyr cys lys gly lys glu cys arg lys his
61/21                                   91/31
ala gln his lys val thr gln tyr lys ala gly lys ala ser leu tyr ala gln gly lys
121/41                                  151/51
arg arg tyr asp arg lys gln ser gly phe gly gly gln thr lys gln ile phe his lys
181/61                                  211/71
lys ala tys thr thr lys lys val val leu arg leu glu cys met ser cys lys thr lys
241/81                                  271/91
thr gln leu ala leu lys arg cys lys his phe glu leu gly gly glu lys lys gln lys
301/101
gly gln ala leu gln phe OPA
```

The property of this protein to confer cycloheximide resistance can be evaluated when it is produced in a specific eukaryotic cell host, naturally sensitive to cycloheximide at μg/ml of cycloheximide when it is introduced in a eukaryotic host, for example the yeast *Saccharomyces cerevisiae* under conditions allowing its expression Sequence I

```
                     AT GGTTAACGTT CCAAAGACCA GAAAGACTTA CTGTAAGGGT

AAGGAGTGCC GTAAGCACGC CCAACACAAG GTTACCCAAT ACAAGGCTGG TAAGGCTTCC

TTGTACGCTC AAGGTAAGAG AAGATATGAC CGTAAACAAT CTGGTTTCGG TGGTCAAACC

AAGCAAATTT TCCACAAGAA AGCTAAGACT ACCAAGAAGG TCGTTTTGAG ATTGGAATGT

ATGTCCTGTA AGACCAAGAC CCAATTGGCT TTGAAGAGAT GTAAGCACTT CGAATTGGGT

GGTGAAAAGA AGCAAAAGGG TCAAGCTTTG CAATTCTGA
``` concentrations higher than a threshold defined as a function of the nature of the host, and when it allows resistance to be produced in this host at a concentration about 5 to 15 fold higher, and preferably about 10 fold higher, than the cycloheximide concentration conferring the natural sensitivity in this host.

In yeasts, in *S. cerevisiae* in particular, this increase in the resistance level is about 10 fold, even 100 fold to 1000 fold higher than the level observed in the wild type strain.

As examples, the order of magnitude of the natural sensitivity of various organisms to cycloheximide is given below:

yeasts *S. cerevisiae:* 1 μg/ml
higher eukaryotic cells: 1 μg/ml
tobacco plants: 10 μg/ml.

Generally, the natural sensitivity of a specific organism is expressed as soon the presence of cycloheximide in the culture medium inhibits the growth and multiplication of the organism When reference is made in this text to a eukaryotic host sensitive to cycloheximide, this reference must be interpreted as designating any eukaryotic organism complying with the above definition in regard to cycloheximide resistance.

A cycloheximide resistance protein according to the invention may also be characterized in that it is encoded in the following nucleotide sequence I (SEQ ID NO:2), by a part of sequence I (SEQ ID NO:2) or by a modified sequence I (SEQ ID NO:2), provided that the protein encoded by the partial sequence or this modified sequence is capable of conferring resistance to a concentration equal to at least 100

The invention also relates to a nucleic acid sequence comprising the sequence coding for the cycloheximide resistance protein in *K. lactis*, this protein being characterized in that it complies with one of the following definitions:

(a) it is a nucleic acid sequence of *K. lactis* of about 5.2 kb capable of conferring cycloheximide resistance to a concentration higher than 1 mg/ml in *K. lactis* or in *S. cerevisiae*, and comprising the restriction sites defined in FIG. 3. The various sites are situated at the following positions:

Sau3A: 0, StuI: +300 bp, PvuII: +600 bp, BglIII: +900 bp, BstXI: +1200 pp, PvuII: +2300, PstI: +2400 bp, PstI: +3000 bp, EcoRI: +3200 bp, HindIII: +3300 bp, EcoRI: +3700 bp, HindIII: +4500 bp, HindIII: +4540 bp, SalI: +5100 bp.

(b) it is a nucleic acid sequence of about 5.2 kb, comprising nucleotide sequence I (SEQ ID NO:2) or hybridizing with the sequence complementary to sequence I (SEQ ID NO:2) under conditions of high stringency (0.1×SSC, 0.1% SDS at 65° C.), and capable of conferring resistance to a cycloheximide concentration higher than 100 μg/ml, and preferably higher than 1 mg/ml, in *K. lactis;*

(c) it is a nucleic acid sequence of about 5.2 kb comprising the following nucleotide sequence II (SEQ ID NO:3) or hybridizing with the sequence complementary to sequence II (SEQ ID NO:3) under conditions of high stringency, and capable of conferring resistance to a cycloheximide concentration higher than 100 μg/ml, and preferably higher than 1 mg/ml, in *K. lactis;*

(d) it is a nucleic acid sequence comprising the nucleotide sequence situated between positions 9 and 2763 of sequence II (SEQ ID NO:3) or a sequence hybridizing with the sequence complementary to sequence II (SEQ ID NO:3) under conditions of high stringency, and capable of conferring resistance to a cycloheximide concentration higher than 100 µg/ml, and preferably higher than 1 mg/ml, in *K. lactis*. When a nucleic acid sequence complying with one of the definitions given above is introduced into a yeast such as *S. cerevisiae*, it confers on this yeast resistance to cycloheximide at a concentration higher than 100 µg/ml, this being advantageously expressed for a cycloheximide concentration higher than 1 mg/ml.

```
SEQUENCE II:

|   10      |   20      |   30      |   40      |   50      |   60
     1 CCTCGAGGTC GACATTCAAG GGTTTAGTAT CCTGAAAACA AAGCTTGTAT AGACAGCCGA 60
    61 CGGTTCTTGG TGACTGTTTG CATCCGTGCA CCATAAAATC TCTCTTAACC ACCCACACAT 120
   121 TGATTTTCGT GTTCAATTGA AATGTGAAAA ATAAAATTGT TTCCCAATTA GGACTATATT 180
   181 CGTCTGTGGG AAAATAACAT TGCCTAGTGG CATTGGTGTG GCCTAACCAG GCCGAATCAC 240
   241 TCACTTTCCA CTAACAGACC TTCCTCCTGG TCGGTCTGGT CTGGGCTACC GGCAGTGTAG 300
   301 TCTCTCTTGC CAACACATTA CGCATTCATG CTTGCTTCTG CCTACTGCTT CCCCGCCCAG 360
   361 GCTAAGCTTG GACGTGCGTA GTCGGGGGGC CAGTAACGCC TGCTCGTCTG GACTTGTTCG 420
   421 CCTTCACTCT TGCTGCCGTC TCTGCTTCGA TGGCTGCCAT TCGGCAATTC TCATCTGGAA 480
   481 GGATTGAACC ACCTTGAATT TTTCAACATT AAAATATTAC ACAAGGAAAG TTCATCATAG 540
   541 TAGATATATC GTATAGTTGA TTGTTATAGC ACCTATTTGT TTCAGTACAT TCAGAAAGCG 600
   601 TAACTCAACA GAGATCAAAT CAGTCACAAT GGGTATGTGA ACAAGATTTA AAATATACCG 660
   661 TGGAGATTGT CAGTGGTTTA TTCGATTTTT GGTATCCTGA GGGAAGAATG GAACGTTTGA 720
   721 AGTTTAGTAC CAAGTGAACA TGAAATGAGC TATGGTTATT AACAGAATA CAGCATTTCA 780
   781 GAGTGAATCA ATGAGAAAAC ACCAACCGTA TTGGAAATTC AGATATTGCA TCGACAAGGG 840
   841 GGGAGAGTTC ATTTGAGTTG GTGAACTATA TCAAAAGATC AGTATTTTGG TCGAAGTATG 900
   901 GACGATTCAC TAGCATAAAA CCCTGTTCAC GCTGGAGGAA GTAATTTGGG TTATTTGTTG 960
   961 TCCCTATGTT TCTTAATTCG GTGTAGTCGA GACAACCTCA GAGAATTGTA TATCAGTGAA 1020
  1021 GTCAACGCTA CACTGACTGA ACATAATTAA CAGGAACTCA GTCGTATTAA CAACTGGGG 1080
  1081 TTCAGATAGC CTGGACCTCC CTATACAATA AGAAGAAGAG AATAGAATTC CTGCAATCAA 1140
  1141 AATAAGCTGG ATGAAGCTAA AGAATATTTT TTTACTAACA TCGACATGTA TCACTATCTT 1200
  1201 ATGATATGTT AATTTCTAAC AGTTAACGTT CCAAAGACCA GAAAGACTTA CTGTAAGGGT 1260
  1261 AAGGAGTGCC GTAAGCACGC CCAACACAAG GTTACCCAAT ACAAGGCTGG TAAGGCTTCC 1320
  1321 TTGTACGCTC AAGGTAAGAG AAGATATGAC CGTAAACAAT CTGGTTTCGG TGGTCAAACC 1380
  1381 AAGCAAATTT TCCACAAGAA AGCTAAGACT ACCAAGAAGG TCGTTTTGAG ATTGGAATGT 1440
  1441 ATGTCCTGTA AGACCAAGAC CCAATTGGCT TTGAAGAGAT GTAAGCACTT CGAATTGGGT 1500
  1501 GGTGAAAAGA AGCAAAAGGG TCAAGCTTTG CAATTCTGAG ATTATCTTTT GGAAGACCAT 1560
  1561 TTGTTACCAA TTTGTCAATT TTTTAACTTT TCTATAAGTA TTACGAATTC ACATATACTC 1620
  1621 TTTCATCACA TTTATAATCT CATATCTGTC ATTTGTATAG TTTAGTCTCC ACTGGGTACT 1680
  1681 TCTTCACTTT GCGATTTGTA TTATACGTAT TCTAAGTATA ATTTTCAGCA GAACGCATAA 1740
  1741 GAGTTTATTA ACAAGAATTG TTTACAAAGA ATAGCGTAGG ACTCAGGCTA CATTATTGAT 1800
  1801 CCTGCAGGCA GTAAAGCTTA CATATGACCT TAGCTAATAT AACATGTACA TACTCACCAT 1860
  1861 GTATACCACT TTTTTCATTC CATTGTCTAA AATATGTTTT CAATATTTGC CAAAATCGCC 1920
  1921 AATTTCATTG GAAAAACAAA AACATCGAAT CAAACTTGTT TTAGAAAACA ACGAACATGA 1980
  1981 AACTATACTG TTAACGTTTA GAGACATATT TCACGTCAAC AAGGCCGTTT GGACGTCGCT 2040
  2041 ACTTCAGCAA CAACACGTAA TGTACGGTGG ATATTCGAAT CAGAAGTACT ATCAACAGCC 2100
```

```
2101  TTCTGGTCGT  CCGAAACGAT  TTTCAGCAAC  AGGGAAACAT  GCCCTTTTCG  GAACCTTCTC  2160

2161  AGCCCATGTT  CAGCACCAAT  TATATGAAAC  AACAAGGATC  ACAGCCGTCT  TACAAGACCG  2220

2221  TCTGACCCAA  CAGCAATCGC  AACCTCAGTC  GCATAATAAT  CAATATTATC  CGAATGGAGG  2280

2281  GTTTACTGAT  GTGCCCAACT  TGAATTATCC  AGCGACTCCA  CCACCAACTC  AAAGCATTTA  2340

2341  TTCACATAAC  AACAACTCTA  ATTCGAAGGT  ATATCAATCC  GCTCAGCATA  CATCTCCCGG  2400

2401  TCAATATTCT  GTTGCCAGTG  AGTCCGGTTT  GTACATCCCG  CCACCACTGC  AGCAACAGCA  2460

2461  GAATGGTCAA  CAGAGTCCTG  TGAGATCGGT  ACATCAACAG  ACACAGCAAA  CACCGCCAAC  2520

2521  ATTTACTCAG  CAACAAAGCT  CTTCCCAACC  TCAGTCACCT  CAACACAATA  CGTTATCATG  2580

2581  CACAGCAGCA  GCAGCAGCAG  CAGCAGCAGC  AACAACAAAC  TCAACAGGCC  CAGCAGCAAG  2640

2641  GACAACGACA  AACTCAGCAA  CAGTCTCAGC  AGCAAGCTCA  ACAACAGAAT  GGATCGGCGA  2700

2701  ATAATTACAT  GTATTTTGAG  AGAAGACCTG  ACCTATTGAC  CAAAACTACC  CAAGACAAAG  2760

2761  CAGATCGAAT  TCCTGCAGCC  CGGGGGATCC  ACTAGTTCTA  GAGCGGCCGC  CACCGCGGTG  2820

2821  GAGCTCCAAT  TCGCCCTATA  GT                                              2842

|   10    |   20    |   30    |   40    |   50    |   60
```

Figure 3:
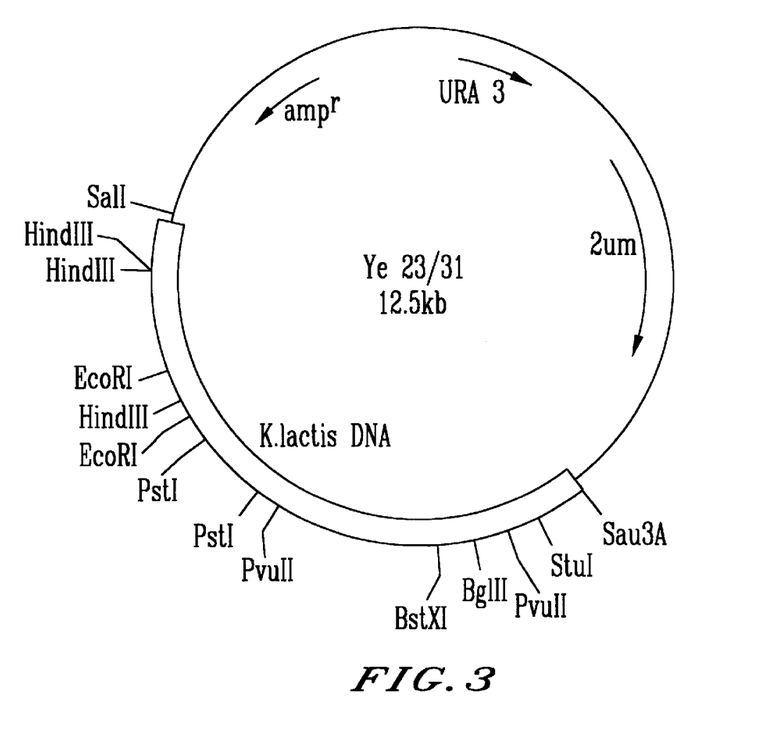
FIG. 3: restriction map of the 5.2 kb DNA fragment of *K. lactis* which was inserted at the BamHI site of the vector Ye 23 (C. Baldari et al., Gene (1985) 35: 27).

According to a preferred embodiment of the invention, the two DNA sequences defined under points (b) and (c) above correspond in addition to the restriction map given in FIG. 3.

According to another preferred embodiment of the invention, the nucleic acid sequence described above is extracted from the *E. coli* strain DH5α recombined with the plasmid Ye23/31, deposited with the CNCM (Collection National de Culture de Microorganismes) in Paris, France in Jul. 2, 1991 under number I-1121.

In this context "complementary sequence" to a given nucleic acid sequence is said to be a reverse and complementary sequence to a given nucleotide sequence. The term "reverse" takes into account the restoration of the 5'-3' orientation of the nucleic acid which is also complementary to the given base sequence by the nature of the nucleatides it contains.

The 5.2 kb nucleic acid sequence comprises, in addition to the sequence coding for the said resistance protein described above, the DNA which may be designated by the term "cofactor", which determines the level of resistance to cycloheximide in *K. lactis* and in a cell host transformed by this sequence. This cofactor DNA is included in sequence II (SEQ ID NO:3).

Thus the invention also relates to the following DNA fragments, included in the 5.2 kb sequence described above:
the BamHI (5')-PvuII (3') fragment of about 2.3 kb
the PvuII (5')-SalI (3') fragment of about 3 kb.

The production of cycloheximide resistance in a given cell host at a defined level can be achieved by transforming this host with a nucleic acid coding for the cycloheximide resistance protein and with a cofactor DNA fragment present in the 5.2 kb sequence, adjacent or not adjacent to the above nucleic acid, the introduction of this fragment in the host being directly correlated with the level of resistance observed. One embodiment of the transformation of a cell host is described in the following pages.

The resistance protein can be isolated by lysis of the *K. lactis* cells followed by the steps desribed in "The Yeasts" (second edition by A. H. Rose and J. S. Harrison, vol. 4: 504–505).

The purification can also be done by affinity using antibodies directed against the sequence A (SEQ ID NO:1). In this case an over-expression of the ribosomal protein is produced which is then purified an polyacrylamide gel according to standard techniques. The molecular weight band corresponding to the sequence A protein is excised. This band is the major band because it results from the over-expression of the protein. It is subjected to reaction with the antibodies, in particular monoclonal antibodies, described above, produced according to standard procedures.

The invention also relates to the ORF A sequence containing nucleic acid I (SEQ ID NO:2)) ORF A being itself included between the nucleotides at positions 1 and 1560 of sequence II (SEQ ID NO:3), it being understood that the sequence included between nucleotides 633 and 1222 corresponds to the intron V. The ORF A sequence contains two exons, one being formed by the nucleotides ATGG situated between nucleotides 629 and 632, the other exon being formed by the sequence included between nucleotides 1223 and 1539.

The nucleotide sequence included between nucleotides 1 and 1539 contains the promoter for the gene, in addition to the ORF A sequence.

Other particularly useful nucleotide sequences in the framework of the invention are the following sequences:
the nucleotide sequence ORF A as such or any nucleotide chain which hybridizing with the sequence complementary to ORF A under the following conditions: 60° C., 2×SSC, 5×Denhart, 0.1% SDS, 0.1 mg/ml salmon sperm DNA,
the coding sequence I (SEQ ID NO:2) (or exon) contained in the ORF A nucleic acid which codes for the resistance protein in *Kluyverormyces lactis*, and included between nucleotides 629 and 1539, which forms a sequence of two exons one of which is included between nucleotides 629 and 632 and the other between nucleotides 1223 and 1539,
the sequence IV, comprising nucleotides 1561 and 2740 and which corresponds to the so-called cofactor sequence situated between nucleotides 1540 and 2763 and capable of increasing the cycloheximide resistance conferred by the resistance protein,
the intron V of ORF A,
the nucleotide sequence III defined by nucleotides 1 and 628, and more particularly by 8 and 628, which contains the regulatory elements of expression for ORF A and in particular the promoter region for the transcription of the ORF A sequence, this promoter contains in particular regulatory regions of the promoters for proteins characteristic of the ribosomes, regions of the "UAS$_{RPG}$" type such as described by W. H. Mager (Biochem. Biophys. Acta (1988) 949: 1–15). These so-called ribosomal proteins are imported into the nucleus of the cell which produces them, where they are assembled into ribosomes, the so-called cofactor sequence IV included between nucleotides 1561 and 2740 which is capable of increasing the resistance to cycloheximide conferred by the resistance protein.

The subject of the invention is also recombinant vectors in particular for cloning and/or expressing the proteins previously characterized.

These expression vectors are characterized by the incorporation, at one of their sites inessential for their replication, of a nucleotide sequence selected from those previously mentioned under the control of the regulatory elements necessary for its expression in a selected eukaryotic cell host, these regulatory elements comprising in particular an optionally inducible promoter and a transcription termination sequence.

Such a vector may comprise a nucleotide sequence coding for a protein called cycloheximide resistance protein, alone or in association with a cofactor nucleotide sequence complying with the previously given definition.

In addition, the invention relates to vectors complying with the above definitions characterized in that they contain in addition a specific heterologous nucleic acid, for example a nucleic acid coding for a protein of industrial or pharmaceutical interest, this nucleic acid being under the control of regulatory elements necessary for its expression in the host, these elements being possibly fused with the sequences controlling the transcription of the nucleotide sequences involved in cycloheximide resistance.

The resistance system according to the invention makes it possible to monitor advantageously the insertion of heterologous sequences such as that of human serum albumin, the surface antigen of hepatitis B virus, with a view to their expression in a eukaryotic host.

As examples, it is possible to use vectors of the replicating plasmid type, integrative vectors such as pSVL (Pharmacia). Such a vector may, for example, contain the nucleotide sequence coding for the protein corresponding to sequence A (SEQ ID NO:1) without its intron.

Generally, it is useful for the implementation of the invention to use multiple-copy vectors, in particular when the transformed cells are eukaryotic cells.

Preferred vectors according to the invention are vectors suited for expression in yeasts, in particular of industrial importance, which it is desired to label with a resistance marker, for example when a auxotrophic marker is not available, a particular yeast being *Pichia pastoris* or *S. pombe*, or vectors suited for expression in a higher eukaryotic animal cell, for example baculovirus, or also vectors suited for expression in a plant cell such as tobacco plants. Thus simian cells or murine cells may be transformed.

A particularly advantageous vector in the framework of the invention is the plasmid Ye23/31 which transforms the *E. coli* strain DH5α deposited with the CNCM an Jul. 2, 1991 under the numbers I-1121.

Furthermore, the invention relates to a eukaryotic cell characterized in that it is transformed by a vector corresponding to the above characteristics and in particular in that it is a yeast cell, for example *Pichia pastoris*, a higher eukaryotic animal cell, for example an insect cell or a mammalian cell, in particular a murine or simian cell, a human cell or also a plant cell.

Such a recombinant cell may be obtained by all of the procedures for the insertion of heterologous sequences commonly used for the preparation of recombinant cell host. It is possible in particular to apply the electroporation procedure described by M. Becker, L. Garente in Methods in Enzymology (1991 vol. 194: 182–187)

It will also be possible to have recourse to the procedures described in the patent application WO 84/02913 on the subject of the insertion in to plant cells of nucleotide sequences heterologous with respect to the nucleic acids naturally contained in such cells.

As an application, the resistance proteins previously described can be used in a selection system corresponding specifically to a cycloheximide-type marker in order to monitor the introduction into a eukaryotic host of a heterologous sequence which it is desired to express in this host. The selection will be the easier if the resistance can be verified with a high concentration of antibiotic, this resistance then resulting from the association of the above resistance protein with a cofactor previously defined.

It is particularly interesting in the framework of the invention to prepare proteins which make it possible to obtain resistance at a cycloheximide concentration of about 100 µg/ml, even 1 mg/ml Furthermore, the invention relates to a procedure for monitoring the presence of a heterologous nucleic acid in a cell host, characterized in that it comprises:

the transformation of the cell host by an expression vector containing at one of its sites inessential for its replication the heterologous nucleic acid, on the one hand, a nucleotide sequence coding for a resistance protein, on the other, and optionally a cofactor nucleotide sequence under the control of the regulatory elements necessary for the expression of these sequences in a selected cell host, the culture of the cell host thus transformed, the placing of the host in contact with a defined concentration of cycloheximide and the detection of host resistance to this antibiotic.

The subject of the invention is also a method for obtaining cells which express cycloheximide resistance as described in the preceding pages, characterized by the following steps:

transformation of a given cell host by a nucleic acid sequence of the invention inserted beforehand in a host plasmid under conditions allowing the expression of the above-mentioned nucleic acid sequence;

culture of the transformed cells (transformants) in a complete medium containing a very low cycloheximide concentration, preferably lower than 2 µg/ml;

recovery of the resistant strains at a cycloheximide concentration higher than 1 to 10 µg/ml.

As an example, in respect to yeasts, the steps described above are performed under the following conditions:

the culture of the transformants is carried out at a temperature between about 29° C. and about 30° C., preferably 30° C., in the presence of a cycloheximide concentration lower than 2 µg/ml for 12 to 36 hours, the strains selected from this culture are those which are resistant culture in the presence of 100 µg/ml of cycloheximide, the complete culture medium contains 10 g/l of yeast extract, 20 g/l of Bacto peptone and 20 g/l of glucose.

The culture step of the transformants mentioned above is preferably carried out for 12 to 18 hours at 30° C., after transformation in a complete liquid medium at sub-limiting concentrations (1 µg/ml). This concentration may be adapted as a function of the strain and the species of yeast used.

In the case of eukaryotic cells as for example (mouse) LTK-cells, the culture medium may be Dulbecco medium supplemented with 10% newborn calf serum and by a fungicidal antibiotic.

The recombinant clones are selected according to the procedure described by Delpeyroux et al. in Journal of Virology (December 1990 vol. 64 (12): 6090–6100).

In summary, the cells are cotransfected with 10 times more recombinant plasmid than vector containing the antibiotic resistance gene G418 (Colbère -Garapin F. et al. 1981, J. Mol. Biol. 150: 1–14). After three weeks, the resistant clones are placed in a culture medium supplemented with cycloheximide at a concentration of 1 to 10 µg/ml.

When the cell host is *S. cerevisiae*, the plasmid containing the nucleotide sequence of the invention may be an episomal multi-copy plasmid of the YEp plasmid family, for example the 2µ plasmid of *S. cerevisiae*, or the episomal multicopy plasmid Ye 23/31.

Other advantages and characteristics of the invention will become apparent from the Examples and Figures which follow.

Figure 1:
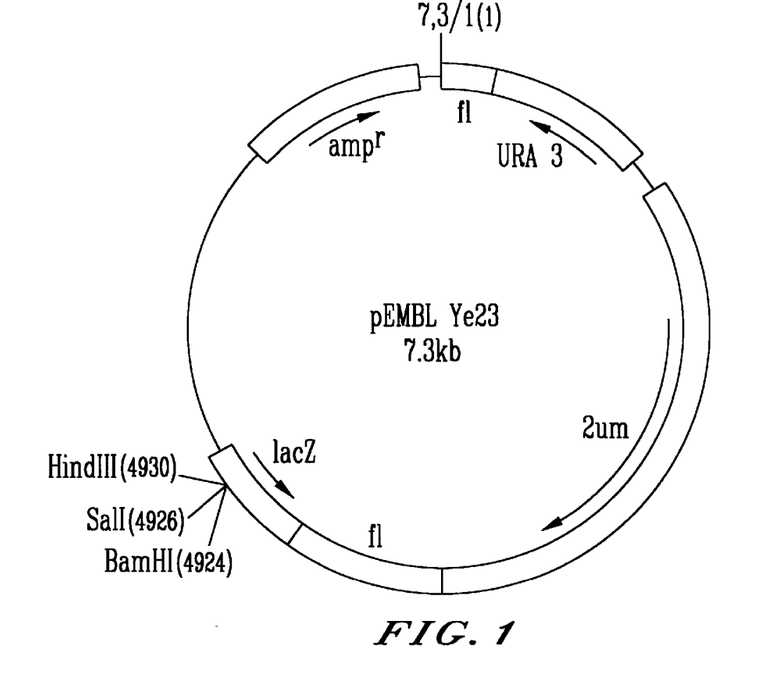
FIG. 1: cloning vector containing the DNA fragment of *K. lactis* of about 5.2 kb conferring cycloheximide resistance.

A genome library of the *K. lactis* strain 2359-152 resistant to several mg/ml of cycloheximide was constructed. This library is constructed in a shuttle vector *E. coli/S. cerevisiae*: pEMBL Ye 23 (Baldari et al. 1985 Gene 35: 27–32, FIG. 1). The chromosomal DNA of *K. lactis* was partially digested by the enzyme Sau3A, then fractionated on a sucrose gradient. The fractions containing DNA included a size between 4 and 9 kb were recovered and the DNA was ligated to the vector YE 23 previously cut and dephosphorylated at the BamHI site situated in the beta-galactosidase gene. This ligation mixture made it possible to transform the *E. coli* strain XL1 and the recombinant transformants were selected an a medium which allows an insertion in the beta-galactosidase gene to be visualized. 23000 recombinant *E. coli* clones were thus selected Restriction analysis of the plasmids of fifty clones enabled the mean size at the DNA insertion in *K. lactis* to be estimated at 5 kb, which gives a 99.5% probability of obtaining a specific gene.

*E. coli* strain XL1 (strain developed by the Stratagene company)
endA1, hsdR17 (rk⁻, mk⁺), supE44, thi⁻, λ⁻, recA1, gyrA96, relA1, Δ (lac), F, proAB, laciq Z M15, Tn10 (tet$^r$)
*S. cerevisiae* strain OL1: α, leu2-3, leu2-112, his3-11, his3-15, ura3-251, ura3-273

The sequenced SalI-PvuII fragment (2.8 kb) contains the ribosomal protein. The various sites are situated respectively at the following positions:
Sau3A: 0, StuI: +300 bp, PvuII: +600 bp, BglIII: +900 bp, BstXI: +1200 bp, PvuII: +2300, PstI: +2400 bp, PstI: +3000 bp, EcoRI: +3200 bp, HindIII: +3300 bp, EcoRI: +3700 bp, HindIII: +4500 bp, HindIII: +4540 bp, SalI: +5100 bp.

EXAMPLES

I—Cloning of the DNA Fragment of *K.lactis* Conferring Cycloheximide Resistance

I.1) Construction of a *K. lactis* Library in *S. cerevisiae*

A genome library of the *K.lactis* strain 2359-152 (WESOLOWSKI et al., 1982, Curr. Genetics 5: 191–197) resistant to concentrations of several mg/ml of cycloheximide was created. This library was constructed in a shuttle vector *E. coli/S. cerevisiae*: pEMBL YE 23 (BALDARI et al., 1985, Gene 35: 27–32) (FIG. 1). *K. lactis* chromosomal DNA was partially digested by the enzyme Sau3A, then fractionated on a sucrose gradient. The fractions containing DNA of a size included between 4 and 9 kb were recovered and ligated to the vector YE 23 previously cut and dephosphorylated at the BamHI site situated in the beta-galactosidase gene, This ligation mixture made it possible to transform the *E. coli* XL1 strain (BULLOCK et al., 1987, Biotechniques 5, 376–379) and the recombinant transformants were selected on a medium which allows an insertion in the beta-galactosidase gene to be visualized. 23000 recombinant *E. coli* clones were thus selected. Restriction analysis of the plasmids of fifty clones enabled the mean size of the DNA insertion in *K. lactis* to be estimated at 5 kb, which gives a 99.5% probability of obtaining a specific gene.

I.2) Transformation of *S. cerevisiae* and Production of Cycloheximide Resistant Transformants The *S. cerevisiae* strain OL1 (BOY-MARCOTTE et al., 1982, Gene 20: 433–440), sensitive to cycloheximide concentrations lower than 1 µg/ml, was transformed with the DNA extracted from the library. In a first stage, the transformants were screened for uracil prototrophy which enabled the total number of transformants to be evaluated. In a second stage these transformants were subcultured on a medium containing cycloheximide at two concentrations: 10 and 100 µg/ml. 3500 URA⁺ transformants were obtained, 7 of which are resistant to cycloheximide concentrations higher than 100 ug/ml. After analysis, it emerged that 6 of the 7 clones retained had integrated the DNA derived from *K. lactis* in to their genome However, in the seventh transformat the resistance character was maintained on the Ye 23/31 plasmid derived from the pEMBLYe23 vector. This transformant is resistant to very high cycloheximide concentrations, in excess of 1 mg/ml. The DNA fragment conferring cycloheximide resistance is about 5.2 kb.

Furthermore for the transformants which have integrated the *K. lactis* DNA fragment into their genome, the resistance phenomenon is maintained in a diploid, heterozygous for this marker. The "cycloheximide resistant" character is thus dominant.

I.3) Protein Responsible for Cycloheximide Resistance

This entire fragment was inserted into pBluescript phagemid vectors (Stratagene). Different unidirectional deletions were constructed with the aid of the enzyme couple ExoIII/S1. The sequencing of the single-stranded DNA was carried out with the aid of the Sanger procedure by using universal primers or primers synthesized in the laboratory from the sequence itself.

Figure 2A:
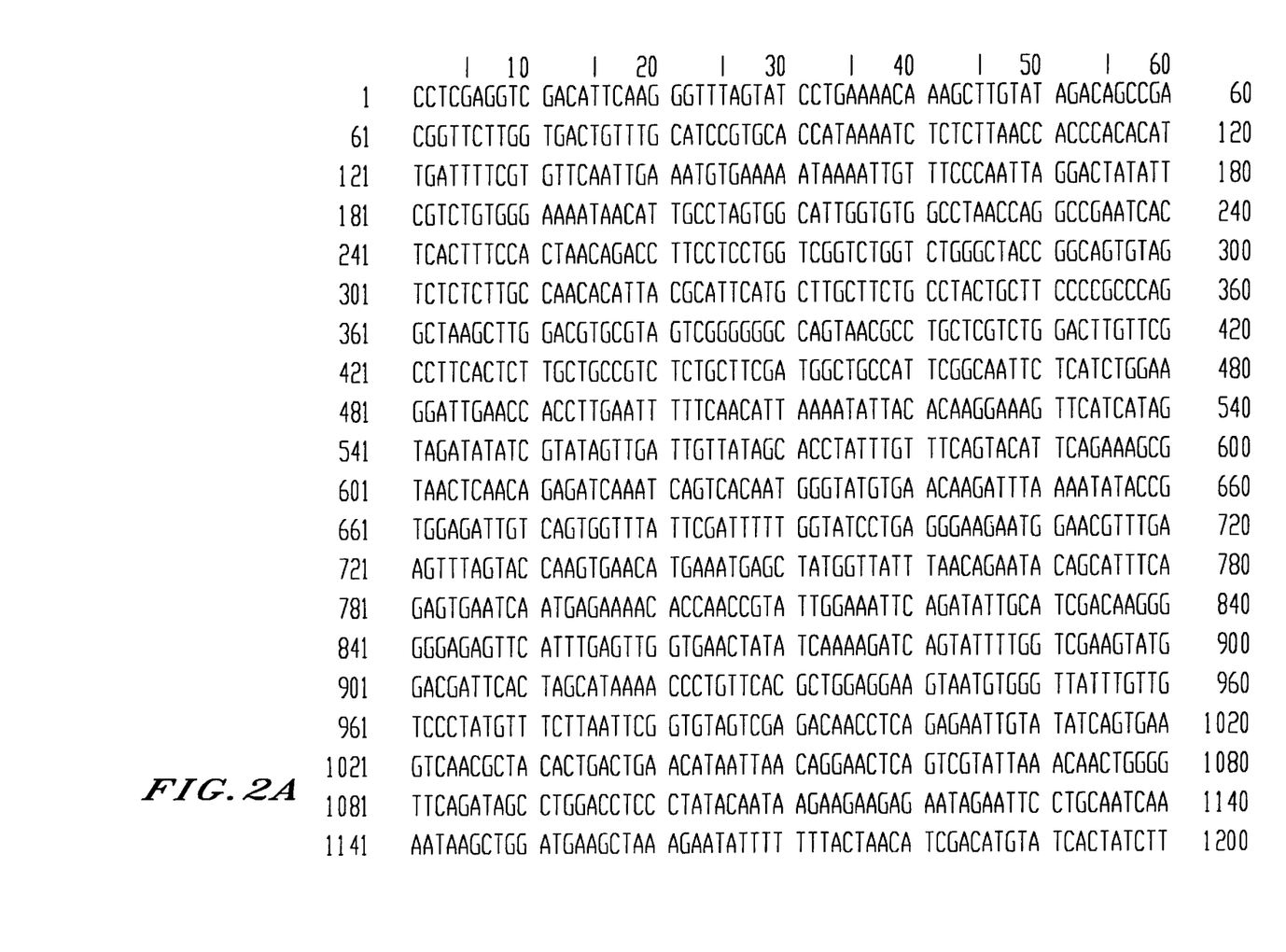
FIG. 2: Sequence fragment of the DNA of *K. lactis* conferring cycloheximide resistance (sequence II (SEQ ID NO:3))
Figure 2B:
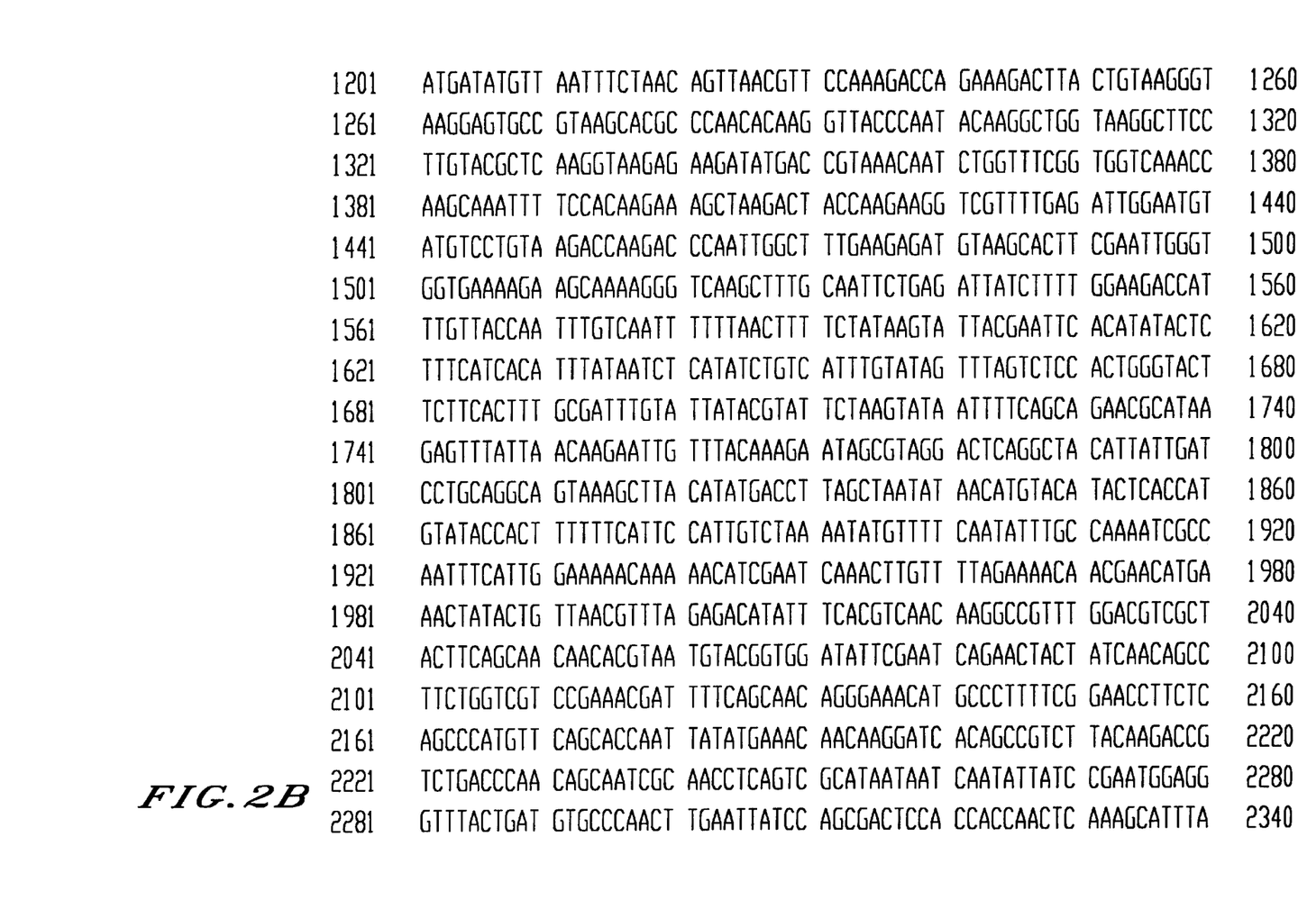
Figure 2C:
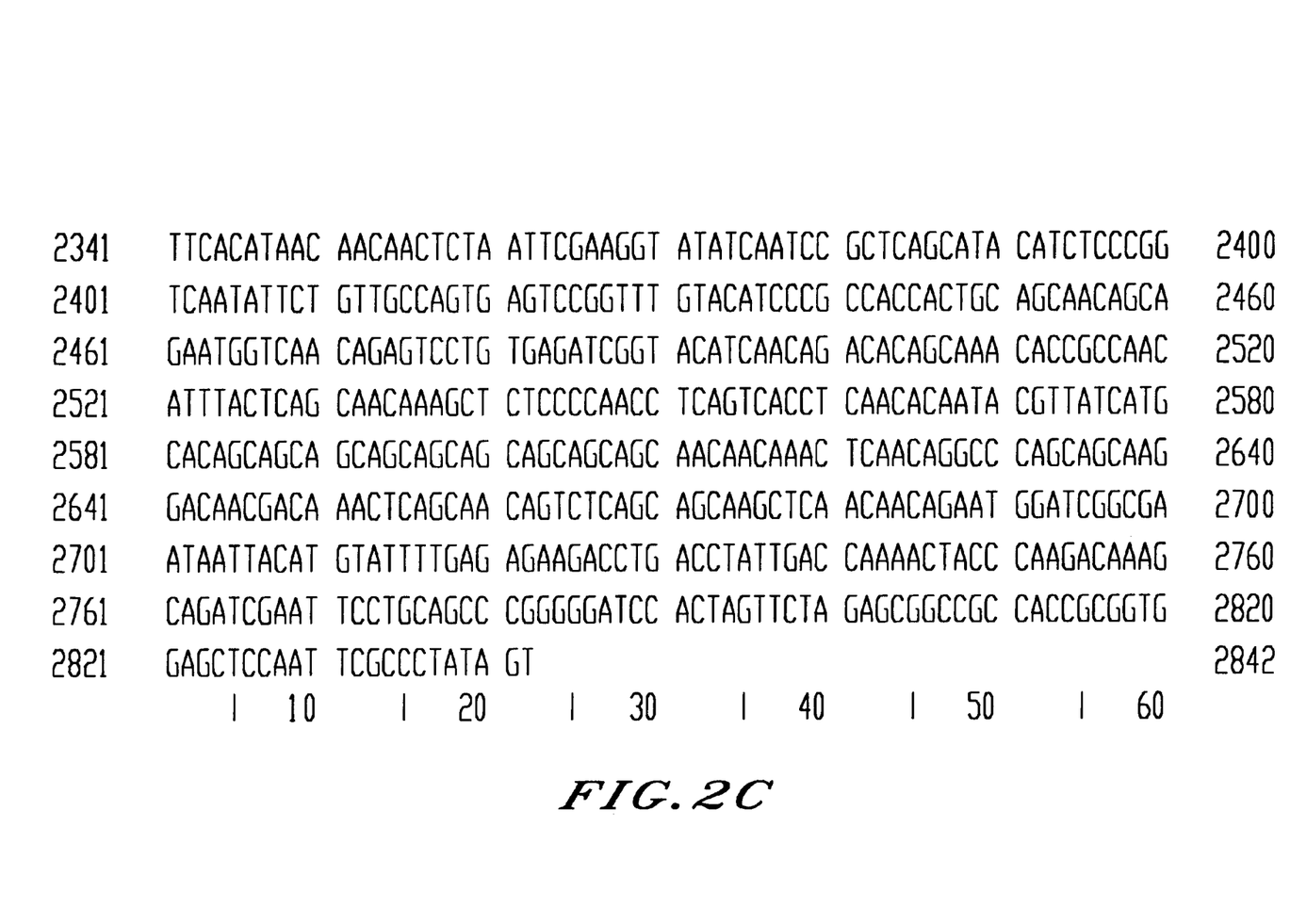

A fragment of the sequence thus obtained is shown in FIG. 2. It contains in particular an open reading frame ORF A.

ORF A

Figure 4:
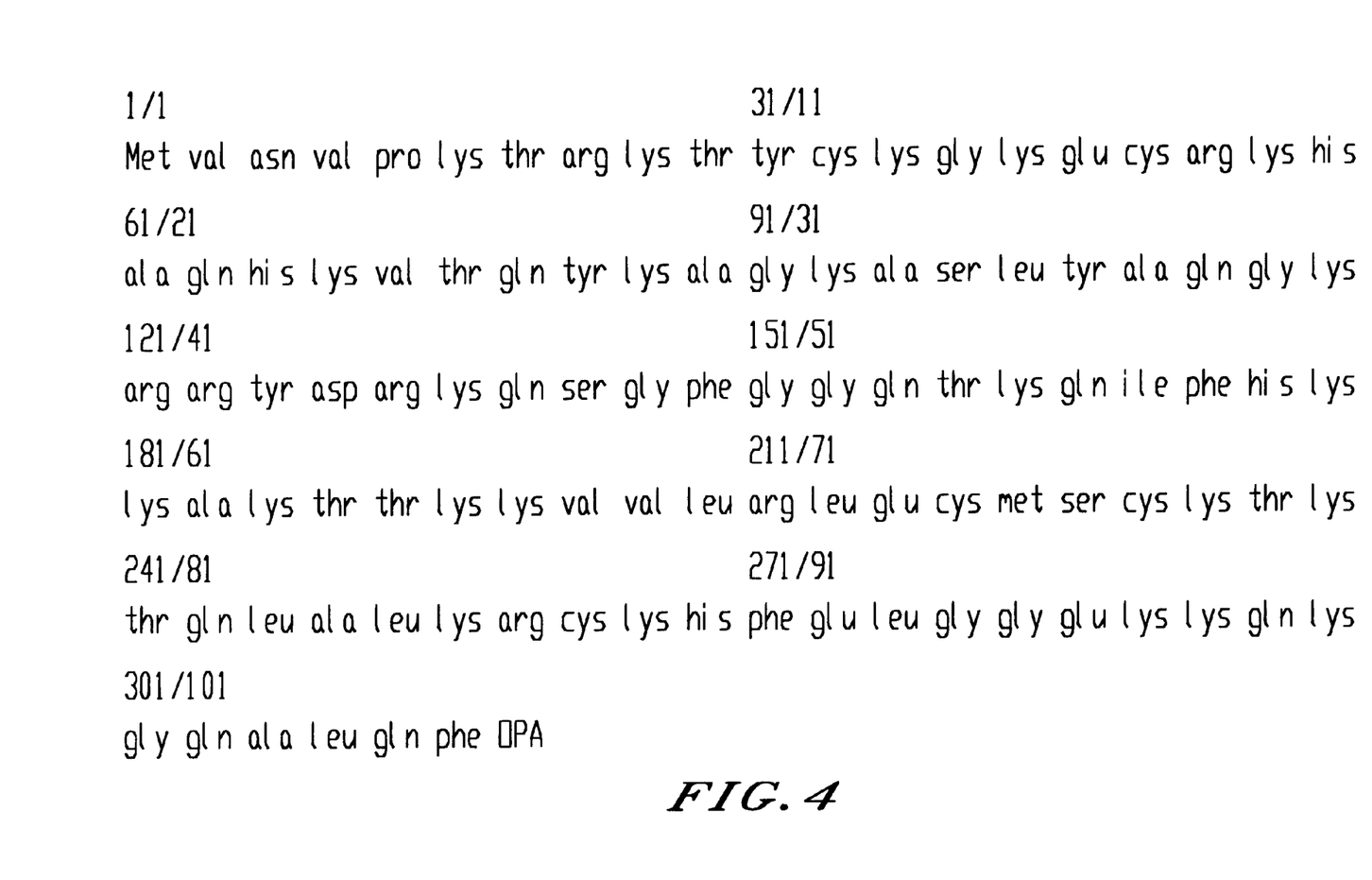
FIG. 4: Protein conferring cycloheximide resistance encoded in *K. lactis* DNA (SEQ ID NO:1).

This open reading frame is 320 bp long (FIG. 2) and carries an intron of 590 bp. This intron is located at the 5' end of the gene, after the first base after the ATG. The protein encoded by the exon contains 150 amino acids (FIG. 4 (SEQ ID NO:1)). The search for homologies with the aid of the EMBL and GENEBANK data banks shows that the ORF A has a 75% homology at the amino acid level with the ribosomal protein L36a of the rat (GALLAGHER et al., 1988, DNA 7: 269–273) and 74% homology with a human ribosomal protein (DAVIES et al., 1986, Gene 45: 183–191) which is itself homologous with the ribosomal protein rp44

(also designated L41) of *S. cerevisiae* (ITOH, 1978 FEBS Lett. 96: 399–402).

This sequence is sufficient to confer a high level of cycloheximide resistance, however, this level is lower than that observed in the transformants possessing the initial 5.2 kb fragment.

I.4) Expression of the Open Reading Frame A

In order to determine to what extent the so-called resistance protein is responsible for the cycloheximide resistance phenomenon, the same *S. cerevisiae* strain was transformed under the same conditions with a vector containing only the ORF A. The transformants which possess the ORF A are resistant to cycloheximide However, the level of resistance observed (100 μg/ml) is about ten times lower than that obtained when the ORF A is associated with the cofactor DNA contained in the entire fragment of 5.2 kb (1000 μg/ml). On the other hand, the deletion of the ORF A sequence leads to the abolition of resistance.

Conclusions

A gene responsible for the phenomenon of cycloheximide resistance was isolated from a DNA fragment of *K. lactis*. This system is composed of a ribosomal protein (ORF A) very closely analogous to the human L36a and rat ribosomal proteins as well as to rp44 (or L41) of *S. cerevisiae*, This protein is necessary to cause the phenomenon of resistance but is not sufficient to have complete resistance to the antibiotic. The presence of a cofactor located on the cloned 5.2 kb fragment of *K. lactis* is necessary to obtain resistance at about the 1 mg/ml level in *K. lactis*.

We claim:

1. A nucleic acid consisting of nucleotides 1–628 of SEQ ID NO:3 or a nucleotide sequence with transcriptional promoter activity, which hybridizes under conditions of high stringency to a sequence complementary to nucleotides 1–628 of SEQ ID NO:3.

2. The nucleic acid of claim 1, consisting of nucleotides 1–628 of SEQ ID NO:3.

3. The nucleic acid of claim 1, consisting of nucleotides 8–628 of SEQ ID NO:3.

4. A vector comprising the nucleic acid according to claim 1.

5. A vector comprising the nucleic acid according to claim 2.

6. A vector comprising the nucleic acid according to claim 3.

7. A vector comprising a nucleic acid according to claim 2 operably linked to a heterologous nucleic acid.

8. A vector comprising a nucleic acid according to claim 2 operably linked to a heterologous nucleic acid.

9. A vector comprising a nucleic acid according to claim 3 operably linked to a heterologous nucleic acid.

10. A eukaryotic host cell, wherein said cell is transformed by a vector according to claim 4.

11. A eukaryotic host cell, wherein said cell is transformed by a vector according to claim 5.

12. A eukaryotic host cell, wherein said cell is transformed by a vector according to claim 6.

13. A eukaryotic host cell, wherein said cell is transformed by a vector according to claim 7.

14. A eukaryotic host cell, wherein said cell is transformed by a vector according to claim 8.

15. A eukaryotic host cell, wherein said cell is transformed by a vector according to claim 9.

16. A nucleic acid comprising a nucleotide sequence which hybridizes to a sequence complementary to nucleotides 1540–2763 of SEQ ID NO:3 under conditions of high stringency, provided that said nucleic acid increases the cycloheximide resistance conferred by a protein of SEQ ID NO:1 on a strain of *Kluyveromyces lactis* transformed with said nucleic acid and a second nucleic acid encoding a protein of SEQ ID NO:1.

17. The nucleic acid according to claim 16, consisting of nucleotides 1540–2763 of SEQ ID NO:3.

18. A method of increasing the cycloheximide resistance conferred by a protein of SEQ ID NO:1 on a strain of *Kluyveromyces lactis*, said method comprising transforming a strain of *Kluyveromyces lactis* with a nucleic acid encoding a protein of SEQ ID NO:1 and a nucleic acid which hybridizes to a sequence complementary to nucleotides 1540–2763 of SEQ ID NO:3 under conditions of high stringency.

* * * * *